United States Patent [19]

Shaw

[11] Patent Number: 4,967,773

[45] Date of Patent: Nov. 6, 1990

[54] NICOTINE CONTAINING LOZENGE

[76] Inventor: Alec S. W. Shaw, Birch House, Off Crimbles Lane, Cockerham, Lancs, England

[21] Appl. No.: 66,494

[22] Filed: Jun. 26, 1987

[30] Foreign Application Priority Data

Jun. 26, 1986 [GB] United Kingdom ............... 8615676

[51] Int. Cl.$^5$ .............................................. A24F 47/00
[52] U.S. Cl. .................................... 131/359; 131/369; 424/197.1
[58] Field of Search ............... 131/359, 369, 366, 367; 424/197.1

[56] References Cited

U.S. PATENT DOCUMENTS

| 46,826 | 3/1865 | Smith | 131/367 |
|---|---|---|---|
| 1,376,586 | 5/1921 | Schwartz | 131/366 |
| 3,845,217 | 11/1974 | Ferno et al. | |
| 3,851,069 | 12/1974 | Hachtman | |
| 4,317,837 | 1/1982 | Kenoe et al. | |

FOREIGN PATENT DOCUMENTS

| 365704 | 7/1969 | Belgium . |
|---|---|---|
| 515895 | 4/1969 | Fed. Rep. of Germany . |
| 835548 | 8/1971 | Fed. Rep. of Germany . |
| 2553332 | 7/1975 | Fed. Rep. of Germany . |
| 1001968 | 11/1962 | France . |
| 1401169 | 5/1965 | France . |
| 524158 | 8/1952 | United Kingdom . |
| 924052 | 8/1953 | United Kingdom . |

OTHER PUBLICATIONS

The Extra Pharmacopoeia Martindale, 28th Edition 1982, pp. 1732–1733 Re: "Nicotine".
The Pharmaceutical Codex, 11th Edition 1979, p. 501 Re: "Lozenges" and pp. 906–908.

Primary Examiner—V. Millin
Attorney, Agent, or Firm—Oblon, Spivak, McClelland, Maier & Neustadt

[57] ABSTRACT

There is disclosed a lozenge formed by compression of at least two mixed components, one of said components including lactose or a lactose containing substance and the other of said components comprising a carrier having nicotine or a nicotine derivative absorbed therein such that there is no direct contact between the nictone and the lactose whilst together in the lozenge.

10 Claims, No Drawings

NICOTINE CONTAINING LOZENGE

This invention concerns a nicotine containing lozenge.

Such lozenges are used by smokers either as a substitute for cigarettes or the like as in no-smoking areas or as an aid in giving up the smoking habit.

One problem with such lozenges is the nausea and discomfort that can follow the ingestion of nicotine or nicotine containing substances.

It is well known that lactose is an effective antidote to nicotine poisoning and the unpleasant symptoms aforesaid.

Hitherto it has not, however, been possible to incorporate lactose or a lactose containing substance into a nicotine containing lozenge since contact between the nicotine and the lactose has caused a reaction destroying the effect of the nicotine It is an object of the present invention to provide a lozenge containing both nicotine and lactose and which overcomes the problem aforesaid.

According to the present invention there is provided a lozenge formed by compression of at least two mixed components, one of said components including lactose or a lactose containing substance and the other of said components comprising a carrier having nicotine or a nicotine derivative absorbed therein such that there is no direct contact between the nicotine and the lactose whilst together in the lozenge.

The component including lactose or a lactose containing substance may be granulated and dried.

The invention will be further apparent from the following description which concerns, by way of example, only a number of nicotine containing lozenges embodying same.

The lozenges are produced by compression of a mixture of at least two components using conventional tablet forming machinery.

The first component is prepared from a mixture of lactose or lactose containing substance and a suitable binder.

A typical formulation for the first component might comprise:

| | |
|---|---|
| Acacia Powder | 1000 gms |
| Lactose | 2900 gms | together with desired flavouring and colouring agents, for example:

| | | |
|---|---|---|
| Liquorice | 1000 | gms |
| Cocoa | 500 | gms |
| Aniseed Flavouring | 37 | gms |
| Peppermint Flavouring | 20 | gms |

If desired, up to 10 kgms of Icing Sugar may be incorporated in the formulation.

The lactose may be replaced by skimmed milk powder, a whey or other milk product.

The acacia powder may be replaced by Avicel microcellulose manufactured by FMC Corporation, USA or a similar gum material.

Any of these formulations may include other additives such as sodium bicarbonate, sodium carbonate or potassium hydroxide or aluminium hydroxide for example.

Water is added to the formulation which is then wet granulated and dried in preparation for addition to the second component.

The second component comprises an inert carrier in which nicotine oil or a nicotine derivative which might conveniently be dissolved in alcohol is absorbed.

One suitable carrier comprises a synthetic silica formulation marketed under the trade name Syloid by W R Grace Limited of North Dale House, North Circular Road, London. This has an average particle size in the range of from 1.5–14 microns and can absorb between 75 and 320% of its own weight of oil.

The carrier and nicotine oil and any other desired additives such as other oils for flavour are gently mixed to cause the oil to be fully absorbed.

The two components are then gently mixed together with a lubricant such as magnesium stearate and compressed into small lozenges.

Each lozenge having a weight of 70–500 mg will typically contain between 0.1 and 8 mg of nicotine preferably in the range of 0.5–2 mg.

Generally, the acacia or Avicel will constitute between 5% and 30% by weight and preferably in the region of 13% by weight of the total dry weight of the finished lozenge.

It will be appreciated that it is not intended to limit the invention to the above example only, many variations, such as might readily occur to one skilled in the art, being possible, without departing from the scope thereof as defined by the appended claims.

For example, the wet granulation and drying steps in the preparation of the first component may be eliminated if pre-granulated lactose is used.

I claim:

1. A lozenge formed by compression of at least two mixed components, one of said components including lactose or a lactose containing substance and the other of said components comprising a carrier having nicotine or a nicotine derivative absorbed therein such that there is no direct contact between the nicotine and the lactose whilst together in the lozenge.

2. A lozenge according to claim 1 wherein said first component comprises lactose or a lactose containing substance and a binder.

3. A lozenge according to claim 2 having between 5% and 30% by weight of said binder therein.

4. A lozenge according to claim 2 wherein said binder comprises acacia powder.

5. A lozenge according to any preceding claim wherein said first component includes one or more of the following ingredients: cocoa, liquorice, aniseed, peppermint, icing sugar.

6. A lozenge according to any preceding claim wherein the first component is wet granulated and dried.

7. A lozenge according to any preceding claim wherein the carrier of said second component comprises a synthetic silica formulation.

8. A lozenge according to any preceding claim having between 0.1 and 8 mg of nicotine therein.

9. A lozenge according to any preceding claim wherein a lubricant is added to the two components before compression thereof.

10. A lozenge formed by compression of at least two mixed components, one of said components including lactose or a lactose containing substance and the other of said components comprising a carrier having nicotine or a nicotine derivative absorbed therein, and additionally containing a lubricant comprising magnesium stearate to facilitate said compression, said two mixed components being such that there is no direct contact between the nicotine and the lactose while together in the lozenge.

* * * * *